(12) United States Patent
Ito et al.

(10) Patent No.: US 9,011,626 B2
(45) Date of Patent: Apr. 21, 2015

(54) METHOD OF MANUFACTURING DISPOSABLE DIAPER

(75) Inventors: Noriaki Ito, Kagawa (JP); Yoshikazu Ogasawara, Kagawa (JP); Satoru Sakaguchi, Kagawa (JP); Tomomi Oku, Kagawa (JP)

(73) Assignee: Unicharm Corporation, Ehime (JP)

( * ) Notice: Subject to any disclaimer, the term of this patent is extended or adjusted under 35 U.S.C. 154(b) by 289 days.

(21) Appl. No.: 13/519,379

(22) PCT Filed: Dec. 27, 2010

(86) PCT No.: PCT/JP2010/073579
§ 371 (c)(1),
(2), (4) Date: Oct. 10, 2012

(87) PCT Pub. No.: WO2011/081139
PCT Pub. Date: Jul. 7, 2011

(65) Prior Publication Data
US 2013/0020017 A1    Jan. 24, 2013

(30) Foreign Application Priority Data

Dec. 28, 2009 (JP) ................... 2009-298310

(51) Int. Cl.
*B32B 38/04* (2006.01)
*A61F 13/15* (2006.01)

(52) U.S. Cl.
CPC ................ *A61F 13/15593* (2013.01)

(58) Field of Classification Search
USPC .................. 156/229, 250, 252, 253
See application file for complete search history.

(56) References Cited

U.S. PATENT DOCUMENTS

| | | | |
|---|---|---|---|
| 5,167,897 A * | 12/1992 | Weber et al. | 264/288.8 |
| 6,361,638 B2 | 3/2002 | Takai et al. | |
| 6,383,431 B1 * | 5/2002 | Dobrin et al. | 264/154 |
| 2001/0008683 A1 | 7/2001 | Takai et al. | |

(Continued)

FOREIGN PATENT DOCUMENTS

| | | |
|---|---|---|
| CA | 2715993 A1 | 8/2009 |
| CN | 1177027 A | 3/1998 |

(Continued)

OTHER PUBLICATIONS

International Search Report and Written Opinion for PCT/JP2010/073579, dated Apr. 5, 2011.

(Continued)

*Primary Examiner* — Mark A Osele
*Assistant Examiner* — Christopher C Caillouet
(74) *Attorney, Agent, or Firm* — Lowe Hauptman & Ham, LLP

(57) ABSTRACT

In a step of performing a stretching process performed by using an embossing roll mechanism, a continuous body of an exterior sheet is conveyed in a state in which strand-shaped members are joined with each of an end region and an end region of the continuous body of the exterior sheet, along a conveyance direction of the continuous body of the exterior sheet; and the strand-shaped members joined with the end region are sandwiched by tooth units of a first embossing roll and interdental units of a second embossing roll corresponding to the end region side, and the strand-shaped members joined with the end region are sandwiched by the tooth units of the first embossing roll and the interdental units of the second embossing roll positioned at the end region side.

5 Claims, 11 Drawing Sheets

(56) References Cited

U.S. PATENT DOCUMENTS

| | | |
|---|---|---|
| 2003/0010423 A1 | 1/2003 | Nakakado et al. |
| 2006/0070701 A1 | 4/2006 | Kobayashi et al. |
| 2008/0210364 A1* | 9/2008 | Schneider et al. ............ 156/167 |
| 2010/0145295 A1 | 6/2010 | Isele et al. |

FOREIGN PATENT DOCUMENTS

| | | |
|---|---|---|
| CN | 1386450 A | 12/2002 |
| EP | 1428487 A1 | 6/2004 |
| EP | 1452157 A1 | 9/2004 |
| EP | 2412352 A1 | 2/2012 |
| JP | 2001509420 A | 7/2001 |
| JP | 2007211386 A | 8/2007 |
| JP | 2007303049 A | 11/2007 |
| JP | 2008012005 A | 1/2008 |
| JP | 2008061691 A | 3/2008 |
| JP | 2009072532 A | 9/2009 |
| WO | 9902114 A1 | 1/1999 |

OTHER PUBLICATIONS

Extended European Search Report issued Jun. 16, 2014, corresponds to European patent application No. 10840995.4.

* cited by examiner

FIG. 4
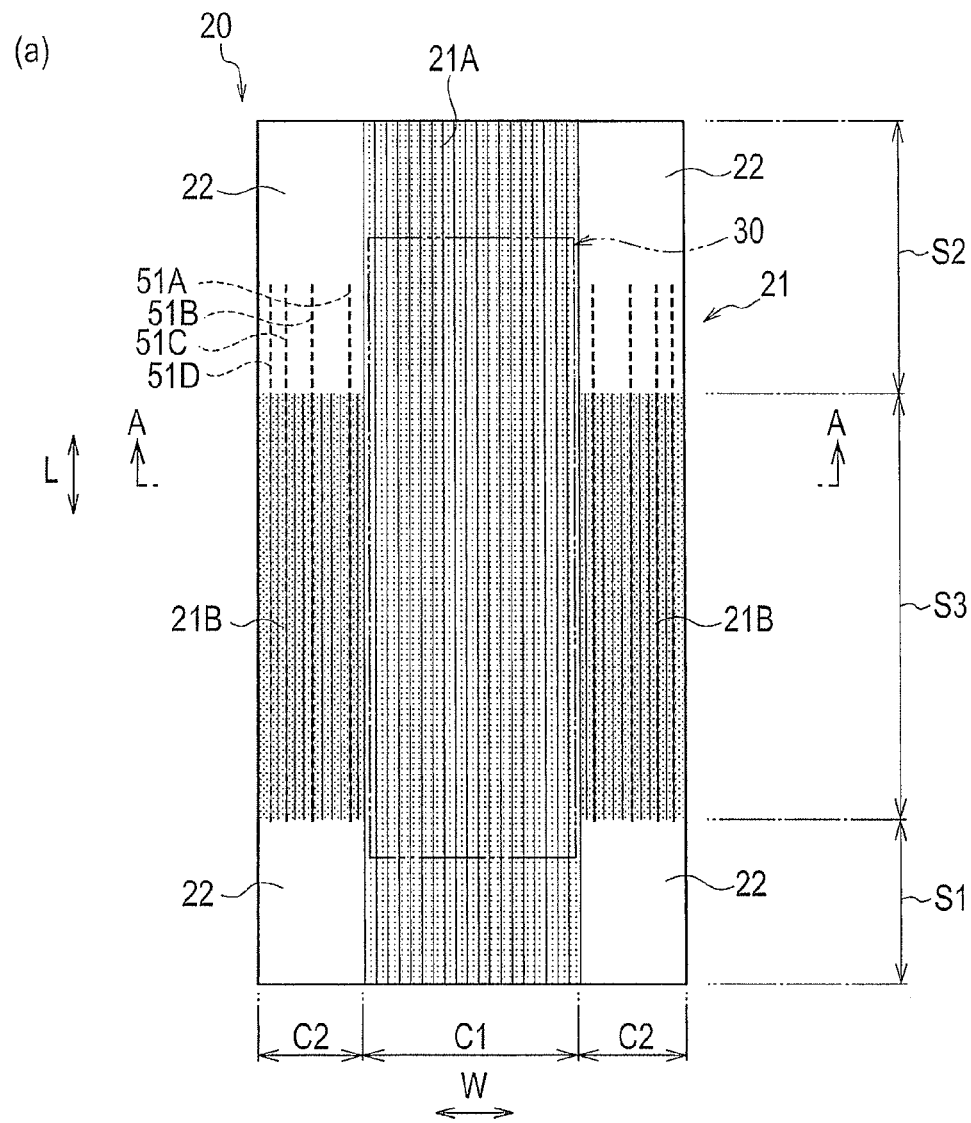
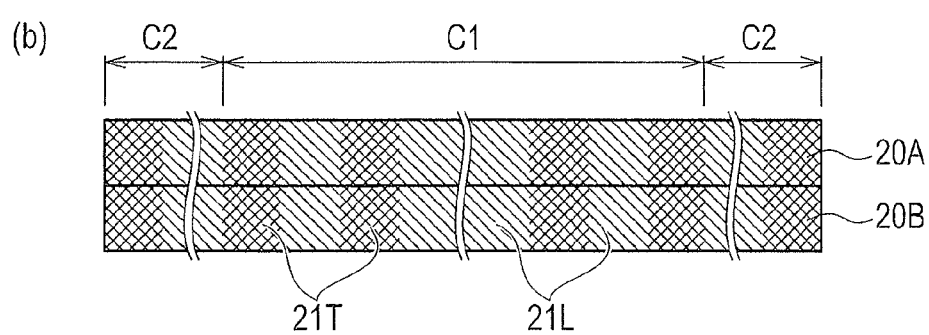

FIG. 12
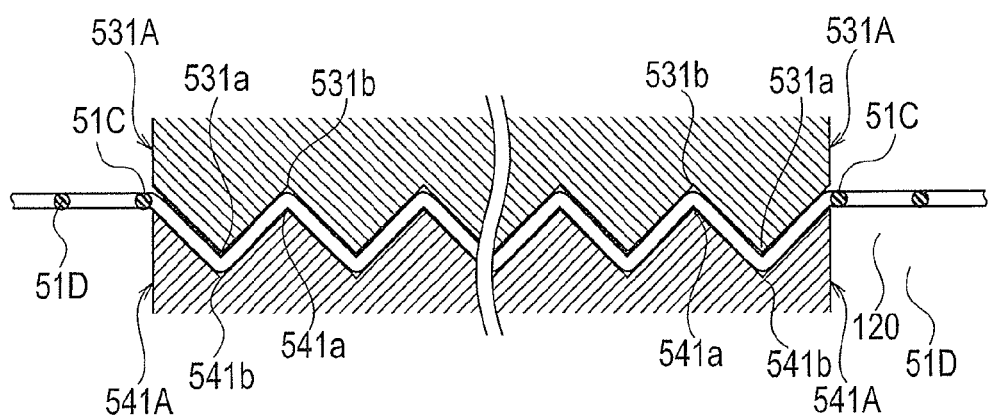
(a)
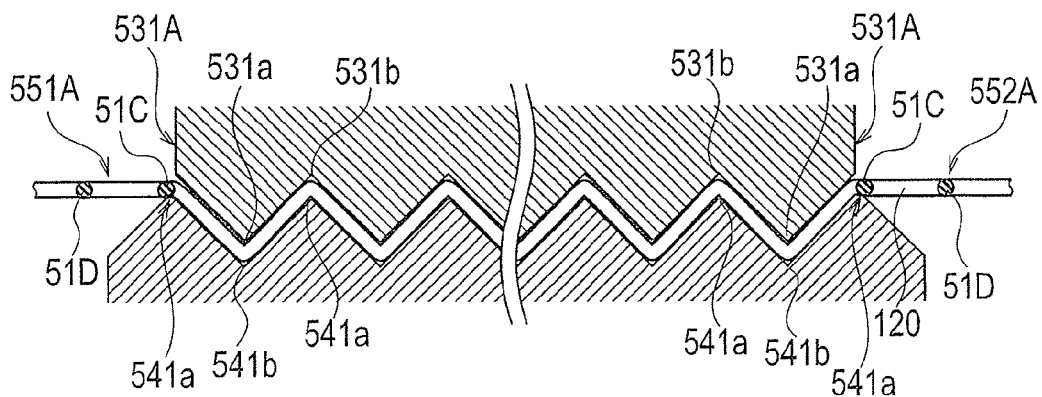
(b)

METHOD OF MANUFACTURING DISPOSABLE DIAPER

RELATED APPLICATIONS

The present application is a National Phase of International Application Number PCT/JP2010/073579, filed Dec. 27, 2010, and claims priority from Japanese Application Number 2009-298310, filed Dec. 28, 2009.

TECHNICAL FIELD

The present invention relates to a method of manufacturing a disposable diaper, by which a disposable diaper is manufactured by performing a process made of softening a continuous body of a liquid-impermeable sheet.

BACKGROUND ART

Conventionally, in an absorbent article such as a pant-type diaper, a liquid-impermeable sheet of polyethylene and the like is used. Generally, the liquid-impermeable sheet is particularly hard even among sheets that configure the absorbent article. Therefore, as compared to a soft sheet, the liquid-impermeable sheet does not easily follow the movement of a wearer, and causes a decline in comfort when the absorbent article is worn.

Therefore, a technique of softening the liquid-impermeable sheet, by reducing the thickness of a continuous body of the liquid-impermeable sheet with the use of an embossing roll mechanism, is known (for example, see PTL 1).

The embossing roll mechanism includes a first embossing roll having a plurality of zigzag shaped first tooth units on a surface along a roll axis direction, and a second embossing roll arranged on the opposite side of the first embossing roll with sandwiching the continuous body, and having a plurality of zigzag shaped second tooth units on a surface along the roll axis direction.

When the continuous body passes between the first embossing roll and the second embossing roll, the continuous body is pressed (embossed) by interfitting of the plurality of second tooth units between the plurality of first tooth units. Because the continuous body is sandwiched between the plurality of first tooth units and the plurality of second tooth units, only the amount of the unevenness of the tooth units is stretched in a thickness direction of the continuous body. The basis weight per unit volume (mass per unit area) of the continuous body declines by stretching, and therefore, the continuous body becomes soft.

CITATION LIST

Patent Literature

[PTL1] Japanese Unexamined Patent Application Publication (Translation of PCT Application) No. 2001-509420 (Pages 16 to 18, FIG. 3)

SUMMARY OF INVENTION

However, the aforementioned conventional technique had the following problem. That is, because a force by which the continuous body is pulled in a conveyance direction is working on the conveyed continuous body, the width of the continuous body (length in the direction perpendicular to the conveyance direction) reduces, and the so-called neck-in phenomenon occurs. Because the continuous body is stretched by the first embossing roll and the second embossing roll in the necked-in state, it was difficult to make a stretching magnification of the continuous body in the widthwise direction uniform.

Therefore, an object of the present invention is to provide a method of manufacturing a disposable diaper by which even a continuous body that necks in easily at the time of conveyance can certainly be stretched uniformly by an embossing roll mechanism, in a method of stretching the continuous body by using the embossing roll mechanism.

In order to solve the above problem, the present invention has the following aspect. That is, the aspect is summarized as a method of manufacturing a disposable diaper (a disposable diaper 1) including a main body (a main body 50) having an exterior sheet (an exterior sheet 20) in which a back nonwoven fabric (a back nonwoven fabric 20B) arranged at the clothing side and a liquid-impermeable back film (a back film 20A) are laminated, a liquid-permeable top sheet (a top sheet 10), and an absorber (an absorber 30) provided between the top sheet and the exterior sheet, including the steps of: performing a stretching process, by which a continuous body of the exterior sheet (a continuous body 120) is stretched in a predetermined region of the continuous body of the exterior sheet: disposing the absorber in the stretched continuous body of the exterior sheet; disposing a continuous body of the liquid-permeable sheet in the continuous body of the exterior sheet in which the absorber is disposed, and then forming a continuous body of the main body; and obtaining individual disposable diapers by cutting the continuous body of the main body, wherein the stretching process is performed by passing the continuous body of the exterior sheet in a state in which the continuous body of the exterior sheet is sandwiched between two rolls (a first embossing roll 530 and a second embossing roll 540) where tooth units (tooth units 531a, 541a) formed on a surface of the rolls and continuing in a circumferential direction of the rolls, and interdental units (interdental units 531b, 541b) formed between the tooth units are formed along a widthwise direction of the rolls in a plurality of columns, and the step of performing the stretching process includes the steps of: joining strand-shaped members (a first strand-shaped member 51A, a second strand-shaped member 51B, a third strand-shaped member 51C and a fourth strand-shaped member 51D), which are string-shaped elastic bodies having elasticity in a conveyance direction of the continuous body of the exterior sheet, with each of a first end region (an end region C301) including an end of the continuous body of the exterior sheet in the widthwise direction, and a second end region (an end region C302) including the other end of the continuous body of the exterior sheet in the widthwise direction, along the conveyance direction of the continuous body of the exterior sheet; and conveying the continuous body of the exterior sheet in a state in which the strand-shaped members joined with the first end region are sandwiched by the tooth units of one roll and the interdental unit of the other roll corresponding to the first end region side, and the strand-shaped members joined with the second end region are sandwiched by the tooth units of one roll and the interdental unit of the other roll positioned at the second end region side.

BRIEF DESCRIPTION OF DRAWINGS

FIG. 4 (*a*) is a plan view of an exterior sheet 20 according to the present embodiment, and FIG. 4 (*b*) is a magnified cross-sectional view (cross-sectional view of A-A of FIG. 4(*a*)) of the exterior sheet 20 according to the present embodiment.

FIG. 12 (*a*) is a magnified cross-sectional view of an embossing roll mechanism 520 for explaining a modification of a position at which a strand-shaped member 51 is sandwiched. FIG. 12 (*b*) is a magnified cross-sectional view for explaining a modification of the first embossing roll 530 and the second embossing roll 540.

DESCRIPTION OF EMBODIMENTS

Figure 1:
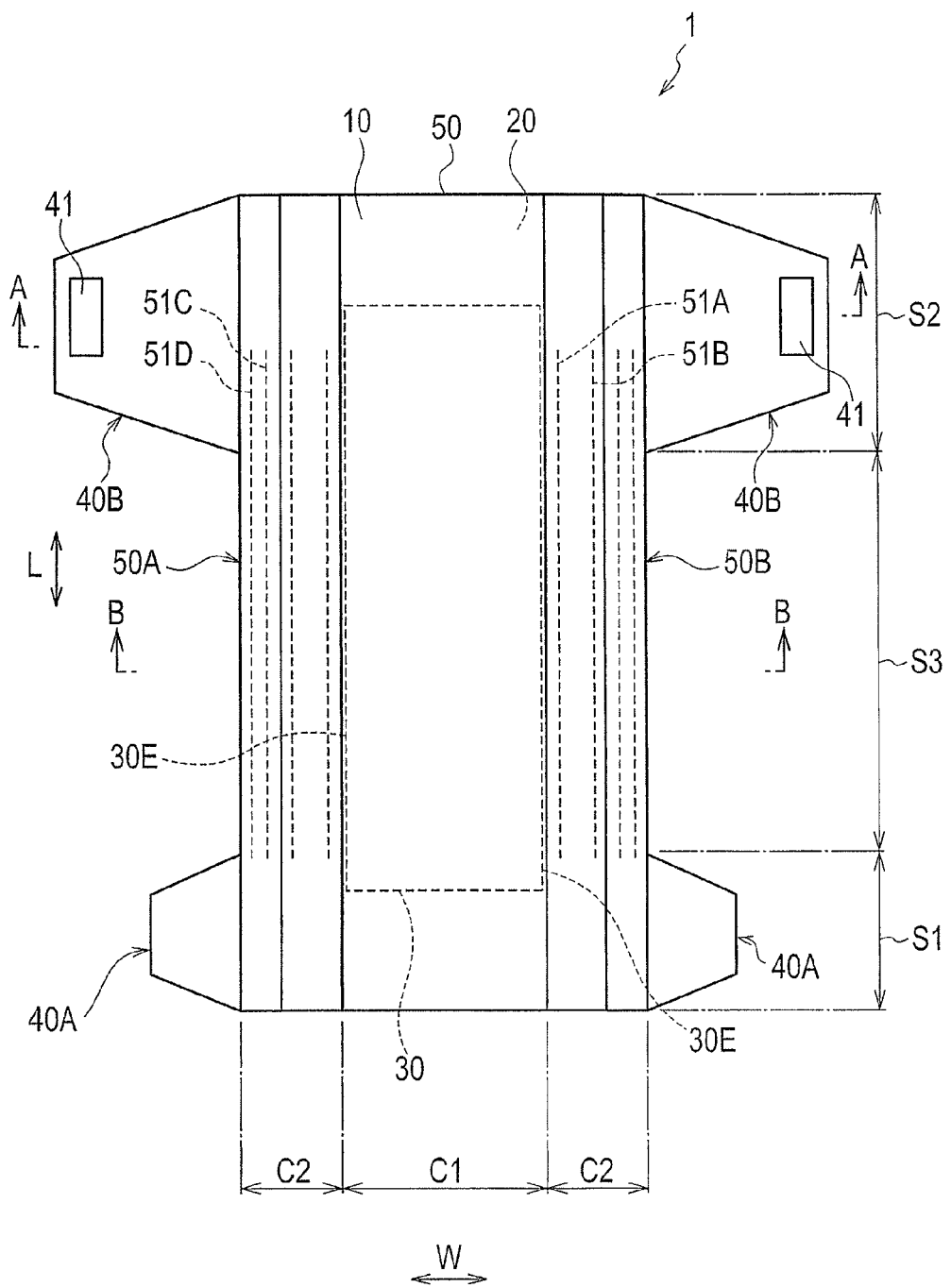
FIG. 1 is a plan view of a disposable diaper 1 according to the present embodiment.

Next, an embodiment of the method of manufacturing a disposable diaper according to the present invention is explained with reference to drawings. In the following description of the drawings, the same or similar reference numerals are used to designate the same or similar parts. It will be appreciated that the drawings are schematically shown and the ratio and the like of each dimension are different from the real ones. Therefore, a specific dimension and the like should be determined in view of the following description. Moreover, among the drawings, the respective dimensional relations or ratios may differ.

(Configuration of the Disposable Diaper)

Figure 2:
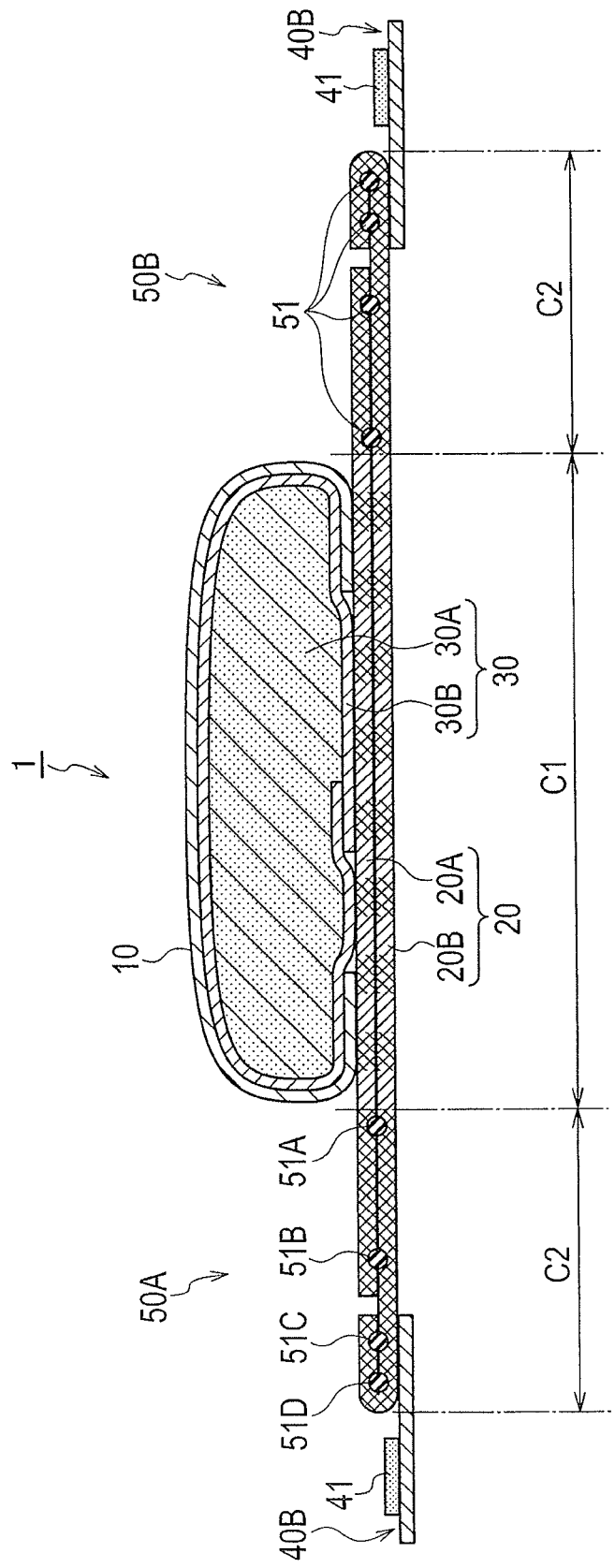
FIG. 2 is a cross-sectional view of the disposable diaper 1 according to the present embodiment.
Figure 3:
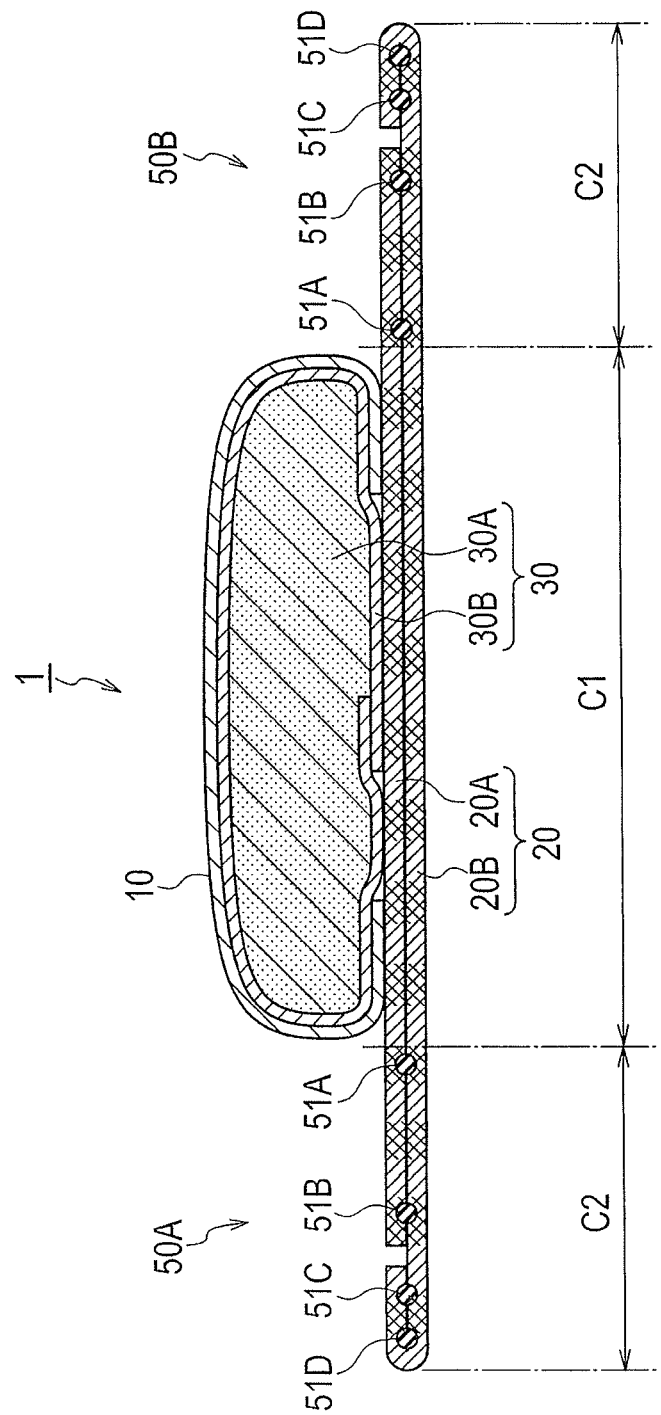
FIG. 3 is a cross-sectional view of the disposable diaper 1 according to the present embodiment.

First of all, a configuration of a disposable diaper 1 manufactured by the method of manufacturing a disposable diaper according the present embodiment is explained with reference to drawings. FIG. 1 is a plan view of the disposable diaper 1 according to the present embodiment. FIG. 2 is a cross-sectional view (cross-sectional view of A-A of FIG. 1) of the disposable diaper 1 according to the present embodiment. FIG. 3 is a cross-sectional view (cross-sectional view of B-B of FIG. 1) of the disposable diaper 1 according to the present embodiment.

The disposable diaper 1 is a tape-type diaper. In the present embodiment, a tape type means a diaper that is in a spread-out state prior to use, rather than being formed in the shape of pants beforehand, and is worn by a wearer by fastening the predetermined portions of the product to each other with a tape and the like.

The disposable diaper 1 has a front waistline region S1 corresponding to the front waistline of the wearer, a back waistline region S2 corresponding to the back waistline of the wearer, and a crotch region S3 corresponding to the crotch of the wearer and positioned between the front waistline region S1 and the back waistline region S2, in a longitudinal direction L of the disposable diaper 1.

The disposable diaper 1 has a central region C1 including an absorber 30 described later, and a pair of side regions C2 positioned outside the central region C1 with respect to a widthwise direction W of the disposable diaper 1, in the widthwise direction W perpendicular to the longitudinal direction L.

The disposable diaper 1 includes a top sheet 10, an exterior sheet 20, and the absorber 30. Here, the top sheet 10, the exterior sheet 20, and the absorber 30 configure the main body 50. The main body 50 of the disposable diaper 1 has a rectangular shape. A pair of ventral side flaps 40A are provided at one end of the main body 50. A pair of dorsal side flaps 40B are provided at the other end of the main body 50.

The top sheet 10 is provided on the side that is in contact with the skin of the wearer. The top sheet 10 enwraps the absorber 30. The top sheet 10 is formed by a liquid-permeable sheet, such as a hydrophilic nonwoven cloth and woven cloth, an aperture plastic film, or an aperture hydrophobic nonwoven cloth.

As shown in FIG. 2, the exterior sheet 20 has a back nonwoven fabric 20B that is in contact with the clothing, and a liquid-impermeable film (hereinafter, called the back film) 20A positioned towards the skin from the back nonwoven fabric 20B and formed by a water-resistive film (for example, polyethylene). The back film 20A is made from a moisture-permeable or moisture-impermeable film. The back nonwoven fabric 20B is a hydrophobic nonwoven cloth configured from an SMS nonwoven cloth, a spun bond nonwoven cloth, or a point bond nonwoven cloth. The back film 20A and the back nonwoven fabric 20B are joined with a hot-melt adhesive and the like.

As an example, the back film 20A of the exterior sheet 20 is a non-breathable film with a basis weight (mass per unit area) of 20 $g/m^2$, and the back nonwoven fabric 20B is made from an SMS nonwoven cloth (composite nonwoven cloth of spun bond nonwoven cloth and melt-blown nonwoven cloth) with a basis weight of 13 $g/m^2$. The hot-melt adhesive that joins the back film 20A and the back nonwoven fabric 20B is desired to be applied by spiral coating to a diameter of 15 mm at 3 $g/m^2$.

As shown in FIG. 2, the absorber 30 is provided between the top sheet 10 and the exterior sheet 20. The absorber 30 absorbs the bodily fluid of the wearer. The absorber 30 is formed from an absorbent core 30A such as ground pulp and high absorbent polymer, and an absorbent sheet 30B, such as a tissue, for covering the absorbent core 30A.

Here, the aforementioned top sheet 10, the exterior sheet 20, and the absorber 30 are joined with each other by an adhesive (for example, hot-melt adhesive) and thermal fusion bonding.

The ventral side flaps 40A and the dorsal side flaps 40B may be a hydrophobic nonwoven cloth, a moisture-permeable or moisture-impermeable film, or a composite sheet formed by pasting together a hydrophobic nonwoven cloth and a moisture-permeable or moisture-impermeable film. As for the ventral side flaps 40A and the dorsal side flaps 40B, a film with the main constituent as polyethylene or polypropylene, a breathable resin film, or a sheet in which a breathable resin film is joined with a nonwoven cloth such as spun bond or spun lace can be used.

As an example, the ventral side flaps 40A and the dorsal side flaps 40B can be formed from a material obtained by joining together two sheets of an SMS nonwoven cloth having a basis weight of 13 $g/m^2$, by embossing or the hot-melt adhesive.

A locking unit 41 configured to lock to the front waistline region S1 is provided in the dorsal side flaps 40B. The locking unit 41 is provided outside the widthwise direction W of the surface at the side where the absorber 30 is provided on the dorsal side flaps 40B. The locking unit 41 is formed by a hook-and-loop fastener and an adhesive tape.

When the locking unit 41 is a hook-and-loop fastener, a female member (not shown in the figure) is provided as a unit to be locked, in the region where the locking unit 41 of the front waistline region S1 is locked. Note that if the front waistline region S1 is configured from a nonwoven fabric, the front waistline region S1 itself can execute the role of the unit to be locked.

Gathers 50A and 50B are formed in the side regions C2 of the main body 50. The gathers 50A and 50B are formed along the longitudinal direction L of the disposable diaper 1, on the outer side of the absorber 30 with respect to the widthwise direction W of the disposable diaper 1. Strand-shaped members 51 are joined to gathers 50A and 50B along the longitudinal direction L of the disposable diaper 1.

In the present embodiment, the strand-shaped members 51 are made from elastic bodies having elasticity (for example, polyurethane rubber). The strand-shaped members 51 are configured from a first strand-shaped member 51A, a second strand-shaped member 51B, a third strand-shaped member 51C, and a fourth strand-shaped member 51D extending from inside the widthwise direction W of the disposable diaper 1 towards the outside. The first strand-shaped member 51A and the second strand-shaped member 51B are provided between the back film 20A and the back nonwoven fabric 20B. The third strand-shaped member 51C and the fourth strand-shaped member 51D are sandwiched by the back nonwoven fabric 20B by folding back of the back nonwoven fabric 20B extending outside the widthwise direction W of the disposable diaper 1 from the back film 20A.

As an example, polyurethane rubber of 620 dtex can be used as the first strand-shaped member 51A and the second strand-shaped member 51B. The polyurethane rubber of 620 dtex is desired to be joined to the exterior sheet 20 by being stretched 2.3 times. Furthermore, polyurethane rubber of 620 dtex can be used as the third strand-shaped member 51C and the fourth strand-shaped member 51D. The third strand-shaped member 51C and the fourth strand-shaped member 51D are desired to be joined to the exterior sheet 20 by being stretched 2.5 times.

The thickness of the strand-shaped members 51 (the first strand-shaped member 51A to the fourth strand-shaped member 51D) is formed smaller than the interval (P1) between the plurality of tooth units 531a and the interval (P2) between the plurality of tooth units 541a of the embossing device 500 (described later) that performs a stretching process on the continuous body 120 of the exterior sheet (see FIG. 10).

(Configuration of the Exterior Sheet)

Next, the aforementioned exterior sheet 20 is explained with reference to drawings. FIG. 4 (a) is a plan view of the exterior sheet 20 according to the present embodiment, and FIG. 4 (b) is a magnified cross-sectional view (cross-sectional view of A-A of FIG. 4(a)) of the exterior sheet 20 according to the present embodiment.

As shown in FIG. 4 (a), the exterior sheet 20 (the back film 20A and the back nonwoven fabric 20B) has a stretched unit 21 and an unstretched unit 22.

The stretched unit 21 is the region in which the exterior sheet 20 is pressed in the thickness direction T of the exterior sheet 20 by the embossing roll mechanism 520 described later. The stretched unit 21 is the region that is formed with a basis weight lesser than the unstretched unit 22 because the stretching process is performed by the embossing roll mechanism 520 described later.

A plurality of columns of unevenness are formed in the stretched unit 21, in continuation to a longitudinal direction L of the disposable diaper 1, in the widthwise direction W of the disposable diaper 1. Strictly speaking, the unevenness may not be formed in the stretched unit 21 in some cases. Traces that help determine that embossing was performed by the embossing device 500 described later are also included in the unevenness.

Specifically, in the stretched unit 21, as shown in FIG. 4 (b), sparse portions 21L with a large amount of stretching and dense portions 21T whose amount of stretching is lesser than the sparse portions 21L are formed alternately. The sparse portions with a large amount of stretching are portions having a large ratio of width of the sheet after stretching with respect to the width of the sheet before stretching.

The stretched unit 21 is desired to undergo the stretching process such that the stretched unit 21 does not become more than 2.5 times with respect to the exterior sheet 20 prior to the stretching process on the exterior sheet 20. The stretched unit 21 has a central stretched portion 21A positioned in the central region C1 within the crotch region S3, and side stretched portions 21B positioned in the side regions C2 within the crotch region S3. That is, the stretched unit 21 is provided in the entire crotch region S3 in the widthwise direction W of the disposable diaper 1. Furthermore, the stretched unit 21 is provided in the entire central region C1 in the longitudinal direction L of the disposable diaper 1.

Figure 5:
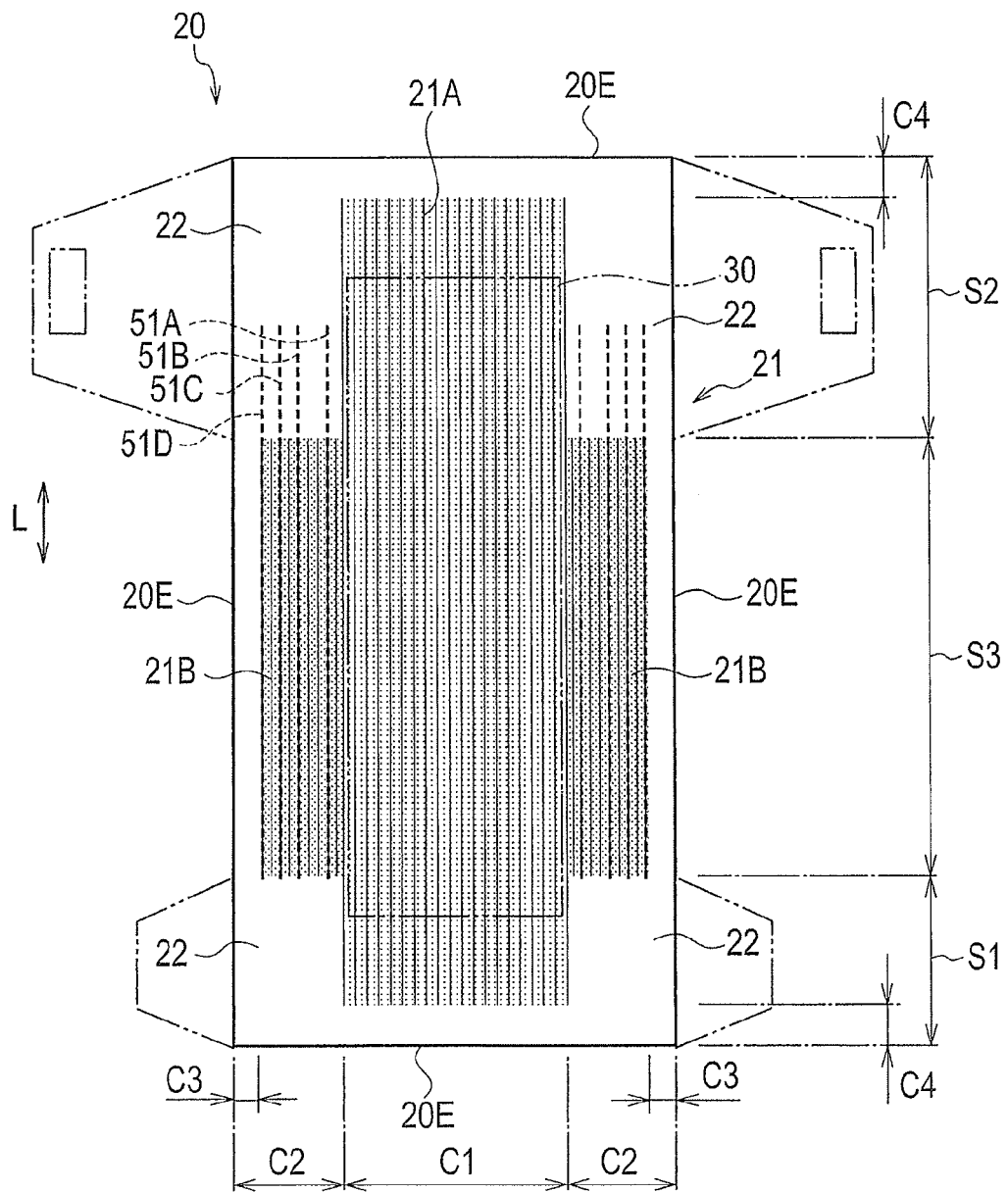
FIG. 5 is a plan view of the exterior sheet 20 according to the present embodiment.

Note that the side stretched portions 21B need not necessarily be provided in the entire crotch region S3, and for example, as shown in FIG. 5, may be provided in the crotch region S3 excluding edge regions C3 and including the edge portions 20E positioned outside the widthwise direction W of the exterior sheet 20, or may be provided in at least a part of the crotch region S3. Similarly, the central stretched portion 21A need not necessarily be provided in the entire central region C1, and for example, as shown in FIG. 5, may be provided in the central region C1 excluding an edge regions C4 and including the edge portions 20E positioned in the longitudinal direction L of the exterior sheet 20, and may be provided in at least a part of the central region C1.

In contrast to the stretched unit 21, the unstretched unit 22 is the region that is not stretched in the widthwise direction W of the disposable diaper 1, and is the region in which the exterior sheet 20 is not pressed in the thickness direction T of the exterior sheet 20. The unstretched unit 22 is the region other than the stretched unit 21

The unstretched unit 22 is provided in at least a part of the front waistline region S1 and the back waistline region S2. That is, the unstretched unit 22 is provided in the pair of side regions C2 in the front waistline region S1, and in the pair of side regions C2 in the back waistline region S2.

(Method of Manufacturing the Disposable Diaper)

Figure 6:
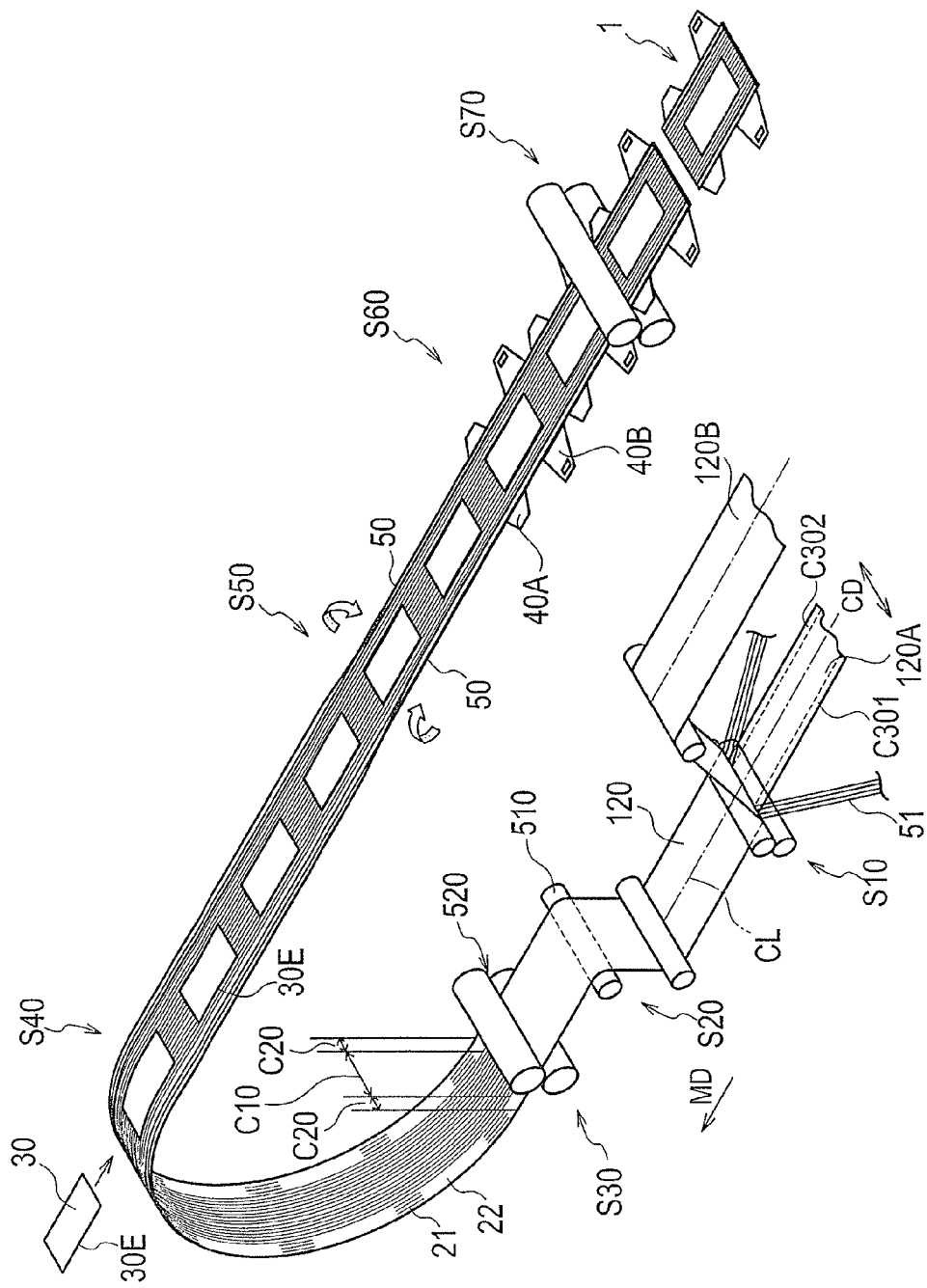
FIG. 6 is a diagram for explaining a method of manufacturing a disposable diaper according to the present embodiment.

Next, a method of manufacturing the aforementioned disposable diaper 1 is explained with reference to drawings. FIG. 6 is a diagram for explaining a method of manufacturing the disposable diaper according to the present embodiment.

The method of manufacturing a disposable diaper according to the present embodiment is a so-called longitudinal-flow method by which the disposable diaper 1 is manufactured while conveying the continuous body 120 of the exterior sheet in a state where the longitudinal direction L of the disposable diaper 1 corresponds to the conveyance direction MD of the continuous body 120 of the exterior sheet 20.

As shown in FIG. 6, the method of manufacturing a disposable diaper includes a sheet-pasting step S10, a sheet-preheating step S20, a sheet-pressing step S30, an absorber-loading step S40, a gather-forming step S50, a side-flap disposing step S60, and a product-cutting step S70. Here, the sheet-pasting step S10, the sheet-preheating step S20, and the sheet-pressing step S30 configure the step in which the stretching process is performed.

In the sheet-pasting step S10, a continuous body 120A of the back film 20A, and a continuous body 120B of the back nonwoven fabric 20B are pasted to each other to form the continuous body 120 of the exterior sheet 20. At this time, the strand-shaped members 51 (the first strand-shaped member 51A to the fourth strand-shaped member 51D) are joined with the continuous body 120 of the exterior sheet (between the continuous body 120A of the back film and the continuous body 120B of the back nonwoven fabric in the present embodiment), along the conveyance direction MD of the continuous body 120 of the exterior sheet. In the present embodiment, the strand-shaped members 51 are joined, in a stretched state, in the conveyance direction MD of the continuous body 120 of the exterior sheet.

Specifically, the strand-shaped members 51 are joined between the continuous body 120A of the back film and the continuous body 120B of the back nonwoven fabric of the end region C301 (first end region) and the end region C302 (second end region) corresponding to the pressed region (region in which the stretching process is performed) in which the continuous body 120 of the exterior sheet is pressed by the embossing roll mechanism 520.

In the sheet-preheating step S20, the continuous body 120 of the exterior sheet is heated at a predetermined temperature (for example, 100° C.) by a preheating roll 510 of the embossing device 500 described later.

In the sheet-pressing step S30, the continuous body 120 of the exterior sheet is conveyed in a state in which the strand-shaped members 51 joined with the end region C301 are sandwiched by the tooth units of one roll and interdental units of the other roll corresponding to the end region C301 side, and the strand-shaped members 51 joined with the end region C302 are sandwiched by the tooth units of one roll and interdental units of the other roll positioned at the end region C302 side.

At this time, the continuous body 120 of the exterior sheet is pressed in the thickness direction T of the continuous body 120 of the exterior sheet. Specifically, the stretched unit 21 (central stretched portion 21A and side stretched portions 21B) is formed in a central region C10 and side regions C20 of the continuous body 120 of the exterior sheet. As a result, the unstretched unit 22 is formed in the pair of side regions C2 of the front waistline region S1, and the pair of side regions C2 of the back waistline region S2 of the disposable diaper 1. The details of the embossing roll mechanism 520 by which the stretched unit 21 is formed in the continuous body 120 of the exterior sheet are described later.

The central region C10 of the continuous body 120 of the exterior sheet corresponds to the central region C1 of the disposable diaper 1 and indicates the region positioned in the center of the widthwise direction CD. The side regions C20 of the continuous body 120 of the exterior sheet correspond to the side regions C2 within the crotch region S3 of the disposable diaper 1, and indicate the regions outside the widthwise direction CD of the continuous body 120 of the exterior sheet from the central region C10.

In the absorber-loading step S40, the absorber 30 in which the absorbent core 30A is covered with the absorbent sheet 30B is loaded (joined) on the continuous body 120 of the exterior sheet on which the expansion process has been performed.

In the gather-forming step S50, by folding back the continuous body 120B of the back nonwoven fabric extended out in the widthwise direction CD of the continuous body 120 of the exterior sheet from the continuous body 120A of the back film, the strand-shaped members 51 are sandwiched by the continuous body 120B of the exterior sheet. The gathers 50A and 50B are thus formed.

In the side-flap disposing step S60, the ventral side flaps 40A formed beforehand, and the dorsal side flaps 40B on which the locking unit 41 is mounted are disposed outside the absorber 30 in the widthwise direction CD of the continuous body 120 of the exterior sheet.

In the product-cutting step S70, the continuous body 120 on which the absorber 30, the dorsal side flaps 40B and the ventral side flaps 40A are disposed is cut in the size of a single product along the widthwise direction CD. The disposable diaper 1 is thus manufactured.

(Configuration of the Embossing Device)

Figure 7:
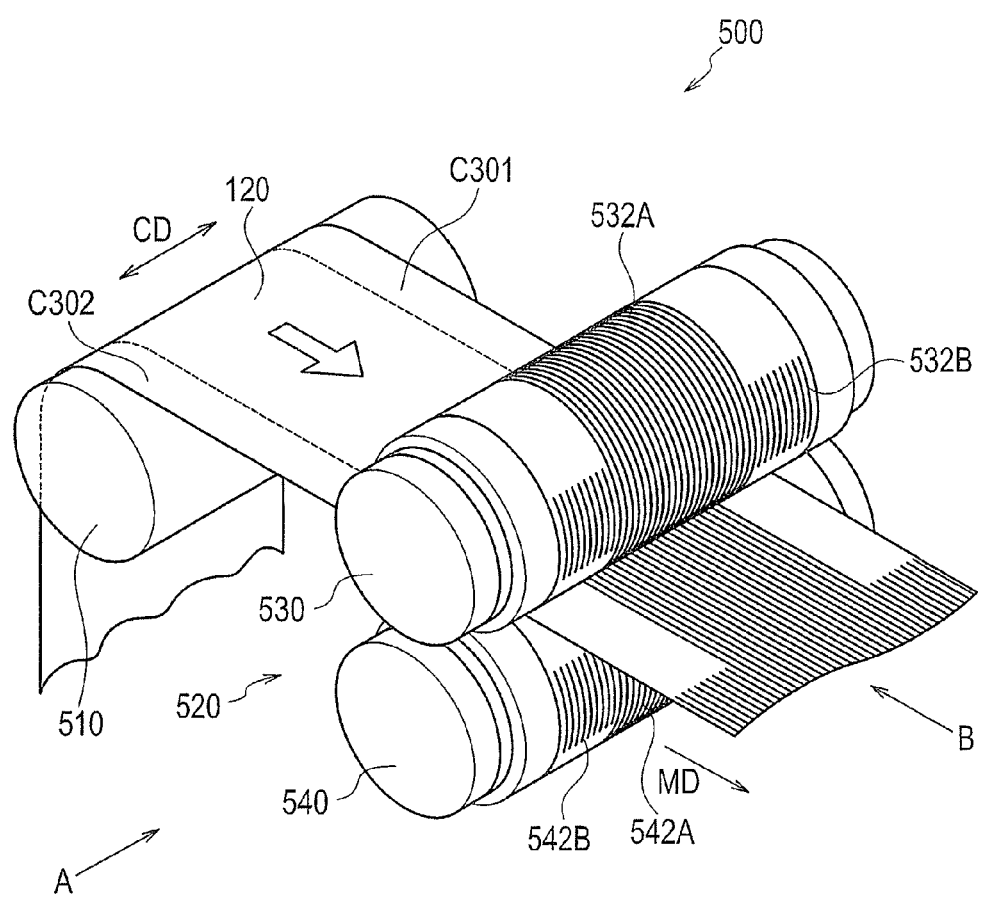
FIG. 7 is a perspective view of an embossing device 500 according to the present embodiment.

Next, the embossing device 500 used in the aforementioned sheet-preheating step S20 and the sheet-pressing step S30 is explained with reference to drawings. FIG. 7 is a perspective view of the embossing device 500 according to the present embodiment.

The embossing device 500 includes the preheating roll 510 and the embossing roll mechanism 520. The embossing device 500 performs a process for stretching the continuous body 120 of the exterior sheet in the widthwise direction CD (called the stretching process) by pressing the continuous body 120 of the exterior sheet in the thickness direction T of the continuous body 120 of the exterior sheet.

The preheating roll 510 is provided upstream of the conveyance direction MD of the continuous body 120 of the exterior sheet from the embossing roll mechanism 520. Before passing through the embossing roll mechanism 520, the preheating roll 510 heats the continuous body 120 of the exterior sheet. The preheating roll 510 is set to a predetermined temperature (for example, 100° C.).

The embossing roll mechanism 520 includes a first embossing roll 530 and a second embossing roll 540. The surface of the first embossing roll 530 includes a central region 532A in which the tooth units that perform the stretching process on the central stretched portion 21A of the exterior sheet are formed, and the side regions 532B in which the tooth units that perform the stretching process on the side stretched portions 21B are formed. Similarly, a central region 542A and side regions 542B are formed in a predetermined region of the surface of the second embossing roll 540 as well.

Figure 8:
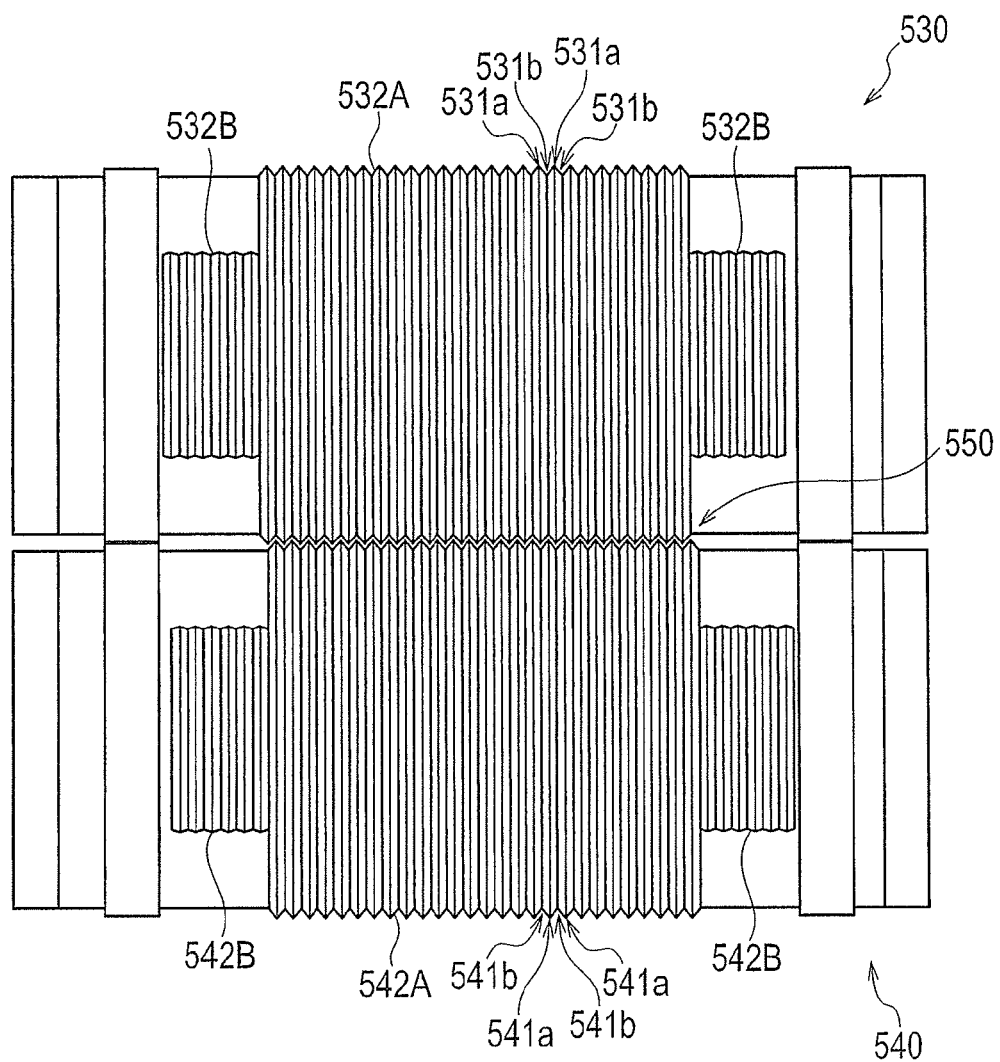
FIG. 8 is a front view of the embossing device 500 according to the present embodiment.

FIG. 8 is a front view (fragmentary view of B of FIG. 7) of the embossing device 500 according to the present embodiment. As shown in FIG. 8, the central region 532A and the side regions 532B of the first embossing roll 530 have the tooth units 531a continuing in the circumferential direction of the first embossing roll 530, and interdental units 531b formed between the tooth units 531a. Multiple columns of the tooth units 531a and the interdental units 531b are formed along the widthwise direction of the first embossing roll 530. The tooth units 531a have a tapered shape (almost triangular shape in the figure) from the outer circumference of the first embossing roll 530 towards the outside, in a cross section along an axial core direction of the first embossing roll 530.

Similar to the first embossing roll 530, the central region 542A and the side regions 542B of the second embossing roll 540 have the tooth units 541a continuing in the circumferential direction of the second embossing roll 540, and interdental units 541b formed between the tooth units 541a. The tooth units 541a are interfitted with the interdental units 531b of the tooth units 531a of the first embossing roll 530 by sandwiching the continuous body 120 of the exterior sheet.

Figure 9:
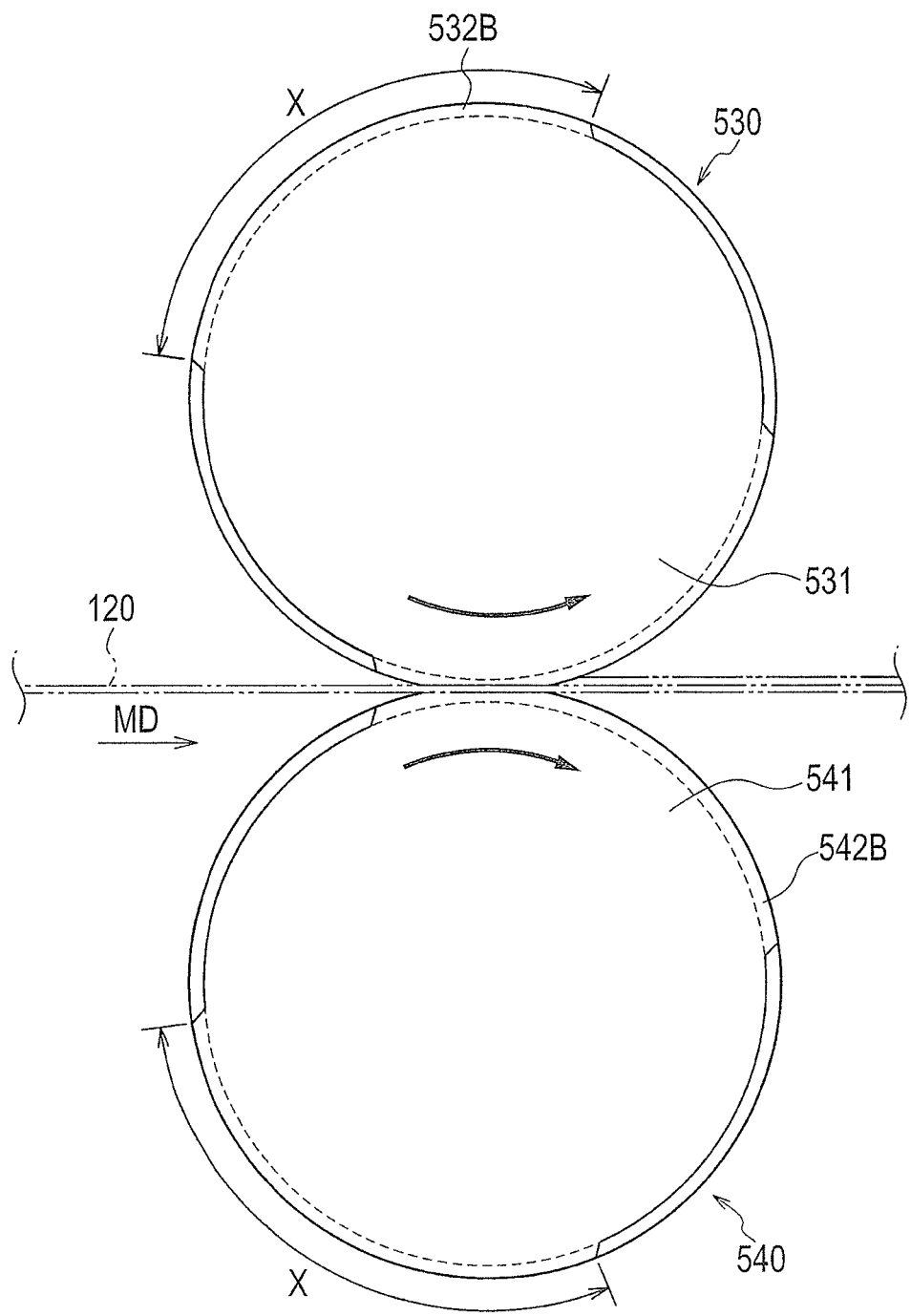
FIG. 9 is a side view of the embossing device 500 according to the present embodiment.

FIG. 9 is a side view (fragmentary view of A of FIG. 7) of the embossing device 500 according to the present embodiment. The length (X) in the roll circumferential direction of the side regions 532B in which the tooth units 531a are formed corresponds to the length of the side stretched portions 21B (that is, the length of the crotch region S3) in the longitudinal direction L of the disposable diaper 1.

Figure 10:
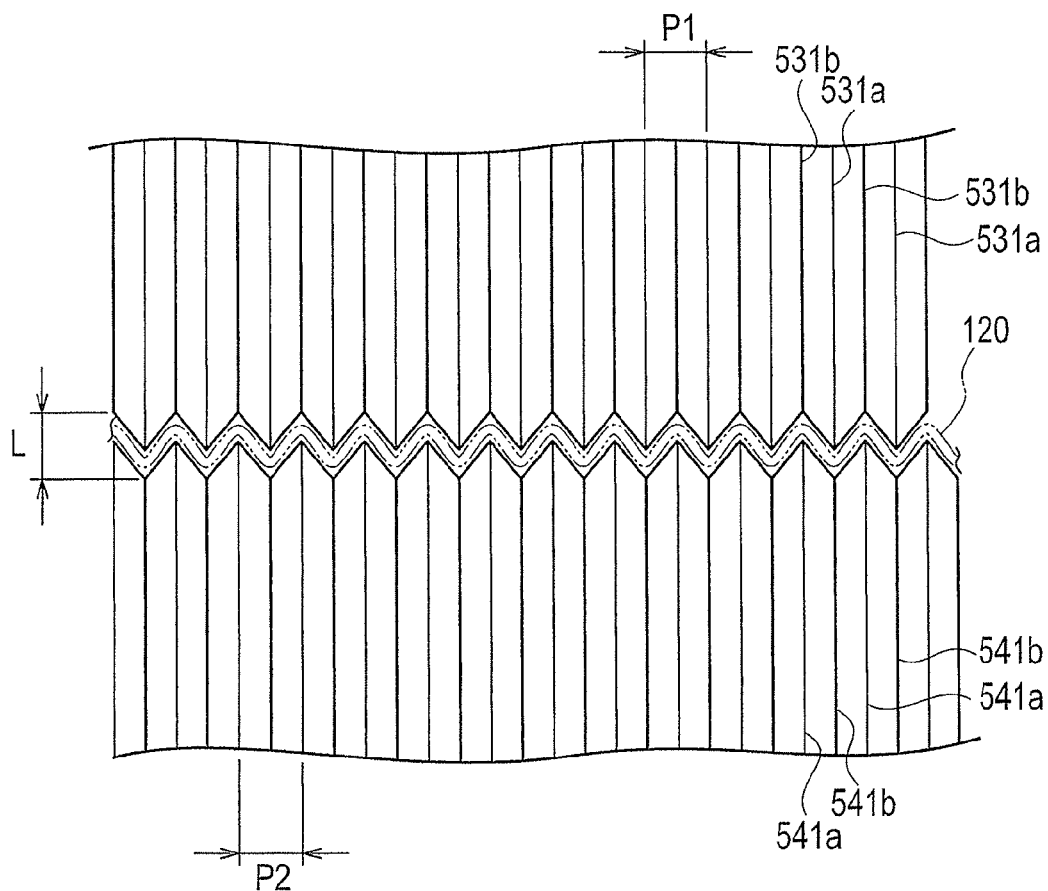
FIG. 10 is a magnified front view of the embossing device 500 according to the present embodiment.

FIG. 10 is a magnified front view of the embossing device 500 according to the present embodiment. As shown in FIG. 10, in the embossing roll mechanism 520 having the aforementioned configuration, the tooth units 541a of the second embossing roll 540 are interfitted with the interdental units 531b that are between the tooth units 531a of the first embossing roll 530, via the continuous body 120 of the exterior sheet. As a result of being sandwiched between the tooth units 531a and the interdental units 531b of the first embossing roll 530, and the tooth units 541a and the interdental units 541b of the first embossing roll 530, the continuous body 120 of the exterior sheet can be stretched by as much as the unevenness (height L) of the tooth units and the interdental units in the thickness direction of the continuous body 120 of the exterior sheet.

For example, the embossing roll mechanism 520 can perform a stretching process on the continuous body 120 of the exterior sheet for expanding the length of the widthwise direction to 2.5 times. The embossing roll mechanism 520 may be set to a predetermined temperature (for example, 50 to 80° C.). For example, when the stretching process is performed by using an embossing roll mechanism 520 in which the diameter of the first embossing roll 530 and the second embossing roll 540 is 127 mm, the unevenness height L of the tooth units 531a and the interdental units 531b is 1.6 mm, and the interval (P1) between the tooth units 531a and the interval (P2) between the tooth units 541a is 2.5 mm, and the preheating roll 510 is set to 100° C., and the embossing roll mechanism 520 is set to 80° C., a stretching process with a stretching magnification as 1.3 times can be performed on the continuous body 120 of the exterior sheet.

Figure 11:
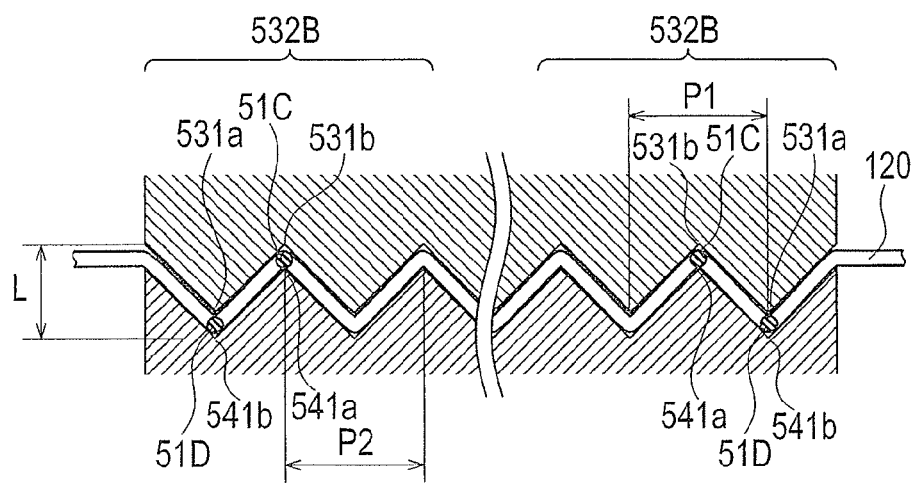
FIG. 11 is a magnified view of the main portion in which both side ends in the widthwise direction of a first embossing roll 530 and a second embossing roll 540 have been magnified.

FIG. 11 is a magnified view of the main portion in which both side ends in the widthwise direction of the first embossing roll 530 and the second embossing roll 540 have been magnified.

According to the embossing roll mechanism 520 of the embodiment, in the stretching process, the continuous body 120 of the exterior sheet is conveyed in a state where the third strand-shaped member 51C and the fourth strand-shaped member 51D joined with the end regions C301, C302 of the continuous body 120 of the exterior sheet are sandwiched by the tooth units 531a of the first embossing roll 530 and the interdental units 541b of the second embossing roll 540.

As an example, in the stretching process of the exterior sheet 20 illustrated in FIG. 5 in which the strand-shaped members 51 are joined with the outer edges of the region in which the stretching process is performed, and along the conveyance direction of the continuous body of the exterior sheet, as shown in FIG. 11, the continuous body 120 of the exterior sheet is conveyed in a state in which the fourth strand-shaped member 51D joined with the outermost side in the widthwise direction of the continuous body 120 of the exterior sheet is sandwiched between the tooth units 531a positioned at the outermost side of the widthwise direction of the first embossing roll 530, and the interdental units 541b of the second embossing roll 540 interfitted with the tooth units 531a.

(Operation and Effect)

In the aforementioned embodiment, the strand-shaped members 51 are joined with the position of the continuous body 120 of the exterior sheet corresponding to each of the end region C301 and the end region C302, in the sheet-pasting step S10. Next, in the sheet-pressing step S30, the continuous body 120 of the exterior sheet is conveyed in a state in which the strand-shaped members 51 joined with the end region C301 are sandwiched between the tooth units 531a of the first embossing roll 530 and the interdental units 541b of the second embossing roll 540, interfitted with the tooth units 531a.

Because the strand-shaped members 51 are string-shaped elastic bodies having elasticity, and are joined with the continuous body 120 of the exterior sheet by being stretched in the conveyance direction MD, a force by which the strand-shaped members 51 are pulled in the conveyance direction is working on the strand-shaped members 51.

Therefore, for example, the strand-shaped member 51C is sandwiched by an inclined plane between the tooth units 531a and the interdental units 531b, and an inclined plane between the tooth units 541a and the interdental units 541b, and thus the strand-shaped member 51 is not conveyed while meandering through an undefined position of the inclined planes. When the strand-shaped members 51 become entrapped in the interdental units 531b or the interdental units 541b, the strand-shaped members 51 become stable at that position.

Therefore, during the sheet-pressing step S30, the continuous body 120 of the exterior sheet that is positioned in the region from the end region C301 up to the end region C302 (for example, the central region C10) has a fixed width. Thus, the stretching magnification of the continuous body in the widthwise direction can be made uniform.

Therefore, according to the method of manufacturing the disposable diaper 1 according to the present embodiment, even for a continuous body that can neck in easily during conveyance, the continuous body can certainly be stretched uniformly by using the embossing device 500. Particularly, because the continuous body 120 of the exterior sheet is conveyed with a fixed width, the stretching process can certainly be performed on the continuous body 120 of the exterior sheet even when the production rate increases. Therefore, a manufacturing failure of the disposable diaper 1 can certainly be reduced.

The continuous body 120 with which the strand-shaped members 51 are joined is desired to be conveyed so as to run along a part of the outer circumference of the first embossing roll 530, for example. Because a force by which the strand-shaped members 51 are pulled in the conveyance direction is working on the strand-shaped members 51, the strand-shaped members 51 become entrapped by themselves in the interdental units 531b where the roll outer diameter is less, in an attempt to pass through the shortest distance. When the strand-shaped members 51 become entrapped in the interdental units 531b, the strand-shaped members 51 become stable at that position. Therefore, during the sheet-pressing step S30, the continuous body 120 of the exterior sheet that is positioned in the region from the end region C301 up to the end region C302 (for example, the central region C10) has a fixed width.

A similar effect is obtained even when the continuous body 120 with which the strand-shaped members 51 are joined is conveyed so as to run along a part of the outer circumference of the second embossing roll 540.

Furthermore, in the method of manufacturing the disposable diaper 1 according to the embodiment, when the strand-shaped members 51 (the fourth strand-shaped member 51D) are joined with the outer edges of the region in which the stretching process of the continuous body 120 of the exterior sheet is performed, and along the conveyance direction of the continuous body 120 of the exterior sheet, the continuous body of the exterior sheet is conveyed in a state in which the fourth strand-shaped member 51D is sandwiched between the tooth units 531a positioned at the outermost side of the widthwise direction of the first embossing roll 530, and the interdental units 541b of the second embossing roll 540, interfitted with the tooth units 531a.

In this way, because the pair of fourth strand-shaped members 51D positioned at the outer edges of the region in which the stretching process is performed are jammed between the tooth units 531a positioned at the outermost side of the widthwise direction of the first embossing roll 530, and the interdental units 541b of the second embossing roll 540 interfitted with the tooth units 531a, the entire surface of the region in which the stretching process is performed can be extended uniformly, and the continuous body 120 of the exterior sheet can more certainly be stretched uniformly.

In the present embodiment, the diameter of the strand-shaped members 51 (the first strand-shaped member 51A to the fourth strand-shaped member 51D) is formed smaller than the interval (P1) between the plurality of tooth units 531a and the interval (P2) between the plurality of tooth units 541a. As a result, the strand-shape members 51 easily become jammed to be entrapped between the adjoining tooth units 531a or the tooth units 541a. Therefore, for example, even when the sheet prior to the stretching process is hard, and the stress for compressing the sheet towards the inner side of the widthwise direction is strong, the stress can be countered sufficiently, and the continuous body 120 of the exterior sheet can certainly be pressed to the planned width.

When the thickness of the strand-shaped members 51 are formed thicker than the interval (P1) between the plurality of tooth units 531a and the interval (P2) between the plurality of tooth units 541a, it becomes difficult for the strand-shaped members to become entrapped between the adjoining tooth units 531a or the tooth units 541a, and the continuous body 120 of the exterior sheet is not pressed uniformly, but a nonuniformity may occur in the continuous body 120 of the exterior sheet.

In the embodiment, the stretched unit 21 is desired to be stretched by 2.5 times or less with respect to the exterior sheet 20 prior to the execution of the stretching process on the exterior sheet 20. If the stretching magnification of the stretched unit 21 is more than 2.5 times, the exterior sheet 20 might become too thin, and damages such as breakage and perforation of the exterior sheet 20 might occur.
(Modification)

The sheet-pasting step S10 and the sheet-pressing step S30 according to the aforementioned embodiment can be changed as described below, for example. The same symbols have been used for the same portions as the embossing device 500 according to the aforementioned embodiment, and mainly, the differences have been explained.

FIG. 12 (a) is a magnified view of the embossing roll mechanism 520 for explaining a modification of a position at which the strand-shaped member 51 is sandwiched. In the modification, the strand-shaped members 51 are joined with the outer side from the region in which the stretching process is performed, and along the conveyance direction of the continuous body 120 of the exterior sheet.

Specifically, as shown in FIG. 12 (a), of the first strand-shaped member to the fourth strand-shaped member, the third strand-shaped member 51C and the fourth strand-shaped member 51D are joined with the outer edges of the region in which the stretching process is performed. The continuous body 120 of the exterior sheet is conveyed in a state where the strand-shaped members 51 (the third strand-shaped member 51C in FIG. 12 (a)) run along the edges of the outer side from the tooth units 531a and 541a formed at the outermost side of the widthwise direction of the first embossing roll 530 and the second embossing roll 540.

That is, the third strand-shaped member 51C is obstructed by the side surface 531A of the tooth units 531a formed at the outermost side of the side regions 532B of the first embossing roll 530, and the side surface 541A of the tooth units 541a formed at the outermost side of the side regions 542B of the second embossing roll 540, and the entrapment in the inner side of the widthwise direction of the continuous body 120 of the exterior sheet is prevented. As a result, the continuous body 120 of the exterior sheet (for example, the central region C10) positioned on the inner side from the third strand-shaped member 51C is maintained at a fixed width.

Rather than cutting the apex of the tooth units 541a of the second embossing roll 540 such that the second embossing roll 540 shown in FIG. 12 (b) matches the side surface 531A of the first embossing roll 530, tooth units 541a are formed even at the end of the outermost side of the widthwise direction as well. Even in this case, same as the example shown in FIG. 12 (a), the third strand-shaped member 51C is obstructed by the side surface 531A of the tooth units 531a formed at the outermost side of the side regions 532B of the first embossing roll 530, and the tooth units 541a formed at the outermost side of the side regions 542B of the second embossing roll 540, and the entrapment in the inner side of the widthwise direction of the continuous body 120 of the exterior sheet is prevented.

OTHER EMBODIMENTS

As described above, the present invention is disclosed through the above embodiments. However, it should not be interpreted that the statements and drawings constituting a part of the present disclosure limit the present invention. From this disclosure, various alternate embodiments, examples, and operation technology will become apparent to one skilled in the art.

For example, the embodiments of the present invention may be altered in the following ways. Specifically, the explanation is based on the fact that the disposable diaper 1 is a tape-type diaper, but the present invention is not limited thereto, and a pant-type diaper, a sanitary napkin, or a panty liner can also be used.

The topsheet 10 and the exterior sheet 20, the absorber 30, and the ventral side flaps 40A and the dorsal side flaps 40B are not restricted to the configuration explained in the embodiment, and can be changed appropriately according to the objective. For example, the explanation is based on the fact that the locking unit 41 provided in the dorsal side flaps 40B is formed from a hook-and-loop fastener, but the locking unit is not limited thereto, and can be formed from an adhesive tape as well.

Furthermore, the exterior sheet 20 is explained as the liquid-impermeable sheet, but the liquid-impermeable sheet is not limited thereto, and a sheet other than the exterior sheet 20 may also be used as long as the sheet does not allow the liquids to pass through. Additionally, the explanation is based on the fact that the strand-shaped members 51 are made from rubber, but the strand-shaped members 51 are not limited thereto, and for example, the strand-shaped members 51 may be sheet-like elastic bodies having elasticity.

The exterior sheet 20 need not necessarily be formed from the back film 20A and the back nonwoven fabric 20B, and may include only the back film 20A.

The ventral side flaps 40A may be formed from the exterior sheet 20 (the back film 20A and the back nonwoven fabric 20B) extending towards the outside of the widthwise direction W of the disposable diaper 1. Similarly to the ventral side flaps 40A, the dorsal side flaps 40B may be formed from the exterior sheet 20 (the back film 20A and the back nonwoven fabric 20B) extending towards the outside of the widthwise direction W of the disposable diaper 1.

The first embossing roll 530 is explained as having the tooth units 531a and the interdental units 531b, but is not limited thereto. Rather than having a cross-sectional shape including triangular tooth units 531a, the first embossing roll 530 may have a cross-sectional shape including rectangular convex portions. The same holds true for the second embossing roll 540.

In the embodiment, the embossing device 500 was explained as an example of forming the stretched unit 21 in the exterior sheet 20, but the embossing device 500 may naturally have other configurations as long as a stretched unit 21 can be formed in the exterior sheet 20. For example, the embossing device 500 need not necessarily include the preheating roll 510 and the embossing roll mechanism 520, and may be configured only from the embossing roll mechanism 520. The configuration of the tooth units 531a and the tooth units 541a can be changed depending on the region in which the stretched unit 21, where the stretching process is performed, is formed, the shape of the region, or else the position of the stretched unit 21.

It has been explained that the shape of the central region 542A and the side regions 542B of the second embossing roll 540 is the same as the shape of the central region 532A and the side regions 532B of the first embossing roll 530. However, the shape need not necessarily be the same as long as the structure is such that the stretched unit 21 can be formed in the exterior sheet 20.

In the embodiment explained by using FIG. 11, the shape may be the same as the shape of the second embossing roll 540 shown in FIG. 12 (b). Additionally, in the example shown in FIG. 12 (b), the structure of the second embossing roll 540 and the structure of the first embossing roll 530 may be opposite.

Furthermore, the method of manufacturing a disposable diaper is not limited to the method explained in the aforementioned embodiment, and an appropriate method can be naturally selected according to the objective, as long as at least the sheet-pasting step S10 and the sheet-pressing step S30 are performed.

Furthermore, in the sheet-pasting step S10, it is explained that the strand-shaped members 51 are disposed between the continuous body 120A of the back film and the continuous body 120B of the back nonwoven fabric, however, the process is not limited thereto, and the strand-shaped members 51 may be pasted to the continuous body 120A of the back film or the continuous body 120B of the exterior sheet, before the sheet-pasting step S10.

Furthermore, in the sheet-pasting step S10, it is explained that the first strand-shaped member 51A through the fourth strand-shaped member 51D are disposed in a stretched state between the continuous body 120A of the back film and the continuous body 120B of the back nonwoven fabric, however, the process is not limited thereto, and at least a pair of strand-shaped members 51 may be disposed. Furthermore, the strand-shaped members 51 need not necessarily be formed by an elastic body, and may be formed by a string and thread other than an elastic body.

As described above, needless to say, the present invention includes various embodiments and the like not described here. Therefore, the technical range of the present invention is to be defined only by the inventive specific matter according to the adequate claims from the above description.

The entire contents of Japanese Patent Application Laid-open No. 2009-298310 (filed on Dec. 28, 2009) are incorporated in the present specification by reference.

INDUSTRIAL APPLICABILITY

According to the present invention, it is possible to provide a method of manufacturing a disposable diaper by which even a continuous body that necks in easily in a direction perpendicular to the conveyance direction, at the time of conveyance, can certainly be stretched uniformly.

REFERENCE SIGNS LIST

1 . . . Disposable diaper, 10 . . . Top sheet, 20 . . . Exterior sheet, 20A . . . Back film, 20B . . . back nonwoven fabric, 20E . . . Edge portion, 21 . . . Stretched unit, 21A . . . Central stretched portion, 21B . . . Side stretched portion, 21L . . . Sparse portion, 21T . . . Dense portion, 22 . . . Unstretched unit, 30 . . . Absorber, 30A . . . Absorbent core, 30B . . . Absorbent sheet, 40A . . . Ventral side flap, 40B . . . Dorsal side flap, 41 . . . Locking unit, 50A, 50B . . . Gathers, 51 . . . Strand-shaped member, 51A through 51D . . . First strand-shaped member through fourth strand-shaped member, 120 . . . Continuous body of exterior sheet, 120A . . . Continuous body of back film, 120B . . . Continuous body of back nonwoven fabric, 500 . . . Embossing device, 510 . . . Preheating roll, 520 . . . Embossing roll mechanism, 530 . . . First embossing roll, 531a . . . Tooth unit, 531b Interdental unit, 532A . . . Central region, 532B . . . Side region, 540 . . . Second embossing roll, 541a . . . Tooth unit, 541b . . . Interdental unit, 542A . . . Central region, 542B . . . Side region

The invention claimed is:

1. A method of manufacturing a disposable diaper including a main body having an exterior sheet, the exterior sheet including a back nonwoven fabric arranged at a clothing side and a liquid-impermeable back film laminated with the back nonwoven fabric, a liquid-permeable top sheet, and an absorber provided between the top sheet and the exterior sheet, said method comprising:

stretching a predetermined region of a continuous body of the exterior sheet;

disposing the absorber on the stretched continuous body of the exterior sheet;

disposing a continuous body of the liquid-permeable top sheet on the continuous body of the exterior sheet on which the absorber is disposed to form a continuous body of the main body; and cutting the continuous body of the main body to obtain individual disposable diapers, wherein the stretching includes:

passing the continuous body of the exterior sheet in a conveyance direction and in a state in which the continuous body of the exterior sheet is sandwiched between two rolls, wherein each of said two rolls, on a surface thereof, includes tooth units extending in a circumferential direction of the roll, and interdental units formed alternatingly with the tooth units in a widthwise direction of the roll;

joining first string-shaped elastic bodies to the continuous body of the exterior sheet at a first end region including an end of the continuous body of the exterior sheet in the widthwise direction along the conveyance direction, and joining second string-shaped elastic bodies to the continuous body of the exterior sheet at a second end region including the other end of the continuous body of the exterior sheet in the widthwise direction, along the conveyance direction of the continuous body of the exterior sheet; and conveying the continuous body of the exterior sheet in a state in which the first string-shaped elastic bodies joined with the first end region are sandwiched between tips of the tooth units of one of the rolls and the corresponding bottoms of the interdental units of the other roll in the first end region, and the second string-shaped elastic bodies joined with the second end region are sandwiched between tips of the tooth units of one of the rolls and the corresponding bottoms of the interdental units of the other roll in the second end region, wherein each of the first and second string-shaped elastic bodies resides in the bottom of the corresponding one of the interdental units.

2. The method of manufacturing according to claim 1, wherein a thickness of the first and second string-shaped elastic bodies is smaller than an interval, in the widthwise direction, between adjacent interdental units of said interdental units.

3. The method of manufacturing according to claim 1, wherein the continuous body of the exterior sheet is not conveyed while at least one of the first and second single string-shaped elastic bodies is sandwiched between inclined surfaces connecting adjacent tips and bottoms of the corresponding tooth units and interdental units.

4. The method of manufacturing according to claim 1, wherein the continuous body of the exterior sheet is conveyed only when the first and second single string-shaped elastic bodies are located at the corresponding tips and bottoms of the corresponding tooth units and interdental units of the rolls, such that the first and second single string-shaped elastic bodies define a fixed width of the continuous body and the stretching is performed uniformly in the predetermined region.

5. The method of manufacturing according to claim 1, wherein each of the two rolls includes a central region and side regions, in the central region, the tooth units and the interdental units continuously extend 360 degrees in the circumferential direction of the corresponding roll, and in the side regions, the tooth units and the interdental units continuously extend less than 360 degrees in the circumferential direction of the corresponding roll.

* * * * *